United States Patent
Shemesh et al.

[11] Patent Number: 5,817,083
[45] Date of Patent: Oct. 6, 1998

[54] MIXING DEVICE AND CLAMPS USEFUL THEREIN

[75] Inventors: Eli Shemesh, Ashdod; Eitan Rogel, Haifa, both of Israel

[73] Assignee: Migda Inc., Englewood Cliffs, N.J.

[21] Appl. No.: 556,931

[22] PCT Filed: May 27, 1994

[86] PCT No.: PCT/US94/06076

§ 371 Date: Mar. 5, 1996

§ 102(e) Date: Mar. 5, 1996

[87] PCT Pub. No.: WO94/27715

PCT Pub. Date: Dec. 8, 1994

[30] Foreign Application Priority Data

May 31, 1993 [IL] Israel ........................................ 105852

[51] Int. Cl.[6] .................................................. A61B 19/00
[52] U.S. Cl. ...................... 604/416; 366/129; 132/384; 604/414; 251/4
[58] Field of Search .................... 604/403, 408, 604/414, 416; 132/219, 221, 222; 251/4; 366/129

[56] References Cited

U.S. PATENT DOCUMENTS

| | | | |
|---|---|---|---|
| 2,663,298 | 12/1953 | Rose | 128/214 |
| 2,775,240 | 12/1956 | Morrisey, Jr. et al. | 128/214 |
| 3,374,509 | 3/1968 | Logan . | |
| 4,386,622 | 6/1983 | Munsch . | |
| 4,396,383 | 8/1983 | Hart . | |
| 4,453,295 | 6/1984 | Laszcsower | 251/10 |
| 4,516,977 | 5/1985 | Herbert . | |
| 4,606,734 | 8/1986 | Larkin et al. | 604/84 |
| 4,607,671 | 8/1986 | Aalto et al. . | |
| 4,610,684 | 9/1986 | Knox et al. | 604/416 |
| 4,834,706 | 5/1989 | Beck et al. | 604/905 |
| 4,902,287 | 2/1990 | Courmen et al. | 604/416 |
| 4,906,103 | 3/1990 | Kao | 604/416 |
| 4,997,430 | 3/1991 | Van Der Heiden et al. | 604/414 |

FOREIGN PATENT DOCUMENTS

| | | |
|---|---|---|
| 091312 | 10/1983 | European Pat. Off. . |
| 142080 | 5/1985 | European Pat. Off. . |
| 91/11152 | 8/1991 | WIPO . |

*Primary Examiner*—Robert A. Clarke
*Attorney, Agent, or Firm*—Ladas & Parry

[57] ABSTRACT

A mixing device for mixing first and second materials, including a container (2) for receiving the first material and having an inlet port (10) and an outlet port (12), a flexible tube (14) having one end connected to the inlet port (10), a cap (16) secured to the opposite end of the flexible tube (14) for attachment to a second container (4) receiving the second material, and a clamp carried by the flexible tube (14) and normally pinching the flexible tube closed, but being manually openable to permit, when the cap (16) has been attached to the second container (4), the addition of the second material in the first container to the first material in the second container and mixing of the two materials together in the first container (2).

11 Claims, 3 Drawing Sheets

MIXING DEVICE AND CLAMPS USEFUL THEREIN

This application is a national filing in the US of International Application PCT/US94/06076 filed May 27, 1994 which in turn claims the priority of Application 105852 filed May 31, 1993 in Israel.

The present invention relates to a mixing device and also to clamp useful therein. The invention is particularly useful in a mixing device for mixing two pharmaceutical ingredients together, such as a drug with a diluent, or a liquid with a powder to be dissolved within the liquid. The invention is therefore described below particularly with respect to such an application.

Many drugs have to be mixed with a diluent or dissolved in a liquid before being administered to a patient. Various techniques and devices are presently used to enable mixing these materials while maintaining sterile conditions where necessary.

An object of the present invention is to provide a mixing device which enables materials to be mixed in an efficient and facile manner and which maintains sterile conditions where necessary.

Another object of the invention is to provide a mixing device which offers protection against tampering before the mixing device is used. A further object is to provide such a mixing device which can be produced in volume and at low cost.

According to the present invention, there is provided a mixing device for mixing first and second materials, comprising: a container for receiving the first material and having an inlet port and an outlet port; a flexible tube having one end connected to the inlet port; a cap secured to the opposite end of the flexible tube for attachment to a second container receiving the second material; and a clamp carried by the flexible tube and normally pinching the flexible tube closed, but being manually openable to permit, when the cap has been attached to the second container, the addition of the second material in the first container to the first material in the second container and mixing of the two materials together in the first container.

According to one preferred embodiment of the invention described below, the clamp includes an indicator element which indicates whenever the clamp has been once opened. According to a second preferred embodiment described below, the clamp includes a severable element which is severed when the clamp is opened thereby not only indicating that the clamp has been once opened, but also preventing reclosing of the clamp. Thus, both embodiments provide tamper-proof protection.

More particularly, in one preferred embodiment described below, the clamp is a slide clamp. The slide clamp is formed with a slot slidably receiving the flexible tube. The slot includes a narrow section which pinches the flexible tube closed when receiving the flexible tube, and a wide section which opens the flexible tube when receiving same. The clamp further includes an indicator element in the form of a membrane covering the wide section of the slot and ruptured when the slide clamp is moved to receive the flexible tube in the wide section of the slot.

In the second described embodiment the clamp is a hinge clamp integrally formed of plastic with two parts hinged together to either a closed position pinching the flexible tube closed, or to an open position opening the flexible tube. The hinge clamp further includes locking elements which are severed whenever the two parts are first moved from their closed positions to their open position.

According to a further feature, the flexible tube may further include a break-away valve which is normally closed but which may be broken away by opening the valve.

As will be described more particularly below, a mixing device constructed in accordance with the foregoing features permits mixing two ingredients in an efficient and facile manner and enables sterile conditions to be maintained whenever necessary. In addition, tamper-proof protection is provided since, by viewing the condition of the indicator on the clamp, the user can be assured that the clamp had not previously been opened, and therefore the materials are in their original, unmixed condition. Such a mixing device is also of very simple structure which can be produced in volume and at low cost.

The invention also provides a slide clamp and a hinge clamp particularly useful in the above mixing device.

Further features and advantages of the invention will be apparent from the description below.

The invention is herein described, by way of example only, with reference to the accompanying drawings, wherein.

Figure 1:
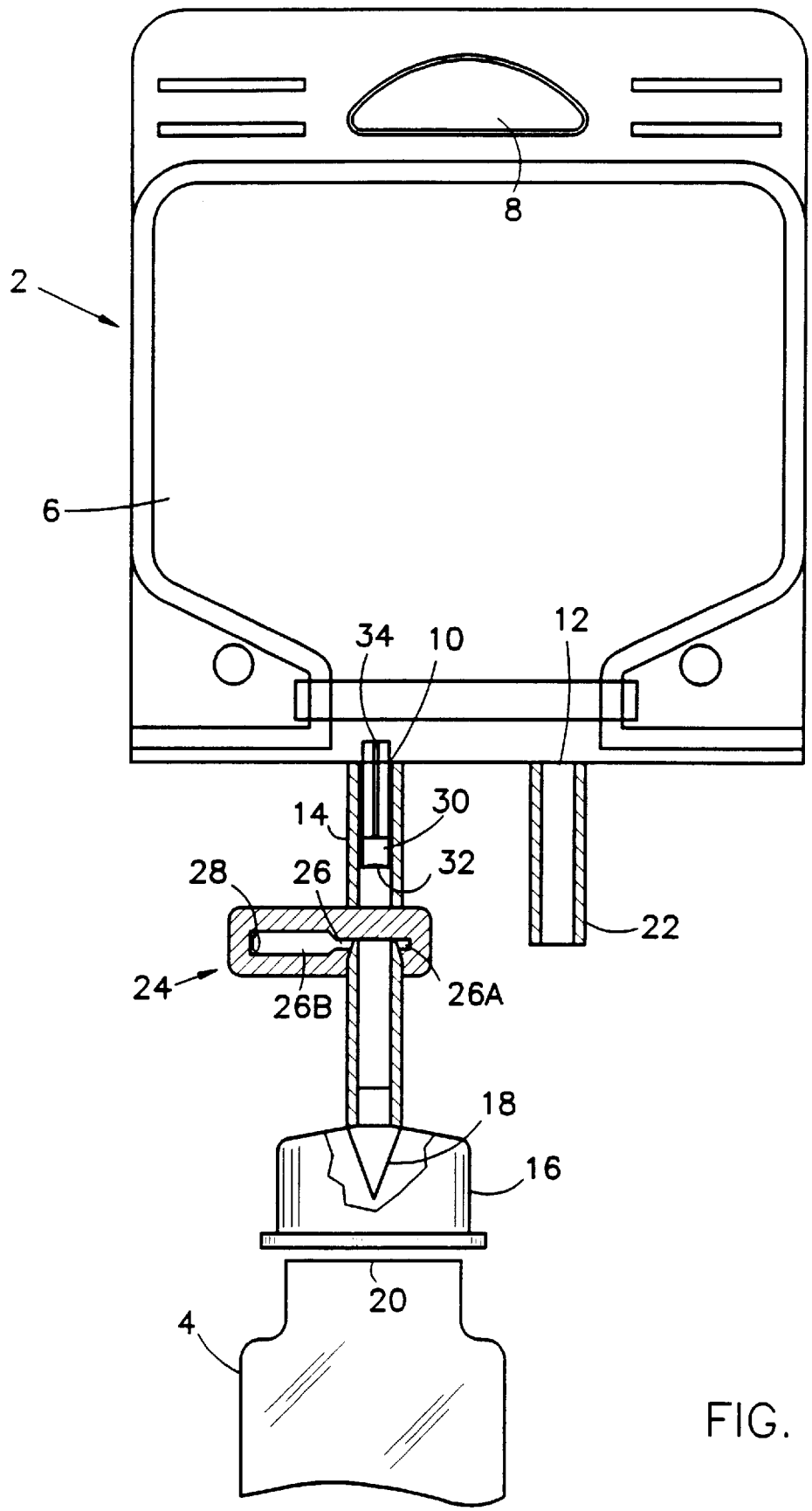
FIG. 1 illustrates one form of mixing device constructed in accordance with the present invention.

The mixing device illustrated in FIG. 1 is particularly useful for mixing a first pharmaceutical material in a first container 2 with a second pharmaceutical material in a second container 4 before the mixture of the two materials is administered to the patient. For example, container 4 may be a plastic or glass vial containing a drug which is to be added to and mixed with a solution, such as a saline solution or a dextrose solution, contained within container 2 before being administered to the patient.

Container 2 may thus be a pliable plastic bag formed with a compartment 6 for the solution, and with an opening 8 at its upper end for suspending the bag while administering the solution and drug therein to the patient.

Plastic bag 2 is further formed with an inlet port 10 and an outlet port 12. A flexible tube 14, e.g., of rubber or plastic, has one end connected to the inlet port 10, and the opposite end connected to a cap 16 adapted to be attached to the vial 4. Cap 16 is further formed with a pointed cannula 18 which automatically pierces a seal 20, (e.g., a septum or plug) covering the mouth of the vial when the cap is attached thereto.

The plastic bag 2 further includes a second flexible tube 22 attached at the outlet port 12 for administering the contents of the bag to the patient.

A clamp 24 is carried by the flexible tube 14 and is normally closed to pinch the flexible tube closed. Clamp 24, however, is manually openable to permit, when cap 16 has been applied to vial 4, the addition of the material within vial 4 into chamber 6 of the plastic bag 2 and the mixing of the two materials together in the latter chamber.

In the device illustrated in FIG. 1, clamp 24 is a slide clamp. It is formed with a slot 26 having a narrow section 26A and a wide section 26B. The narrow section 26A normally receives the flexible tube 14 and pinches it closed, but the clamp may be slid (rightwardly, FIG. 1) to receive the flexible tube 14 within the wide section 26B of slot 26, whereupon the wide section of the slot permits the flexible tube to open.

Slide clamp 24 illustrated in FIG. 1 includes an indicator element which indicates whenever the slide clamp has been moved to its open position. This indicator element is in the form of a membrane 28 which covers the wide section 26B of the slot, and which is automatically ruptured whenever the slide clamp has been moved to its open position with the slot wide section 26B receiving the flexible tube 14.

The mixing device illustrated in FIG. 1 further includes a break-away valve 30. Valve 30 normally closes the flexible tube 14 but may be broken away to open the tube to the flow of material from one container to the other.

For this purpose, valve 30 is secured within flexible tube 14 by a membrane 32 at one side of the valve 30 and normally blocking the flexible tube. The other side of valve 30 carries a rigid stem 34 which may be manipulated by the user in order to rupture the membrane 32 and thus open the flexible tube for introducing the material from vial 4 into the plastic bag 2.

The manner of using the mixing device illustrated in FIG. 1 will be apparent from the above description. Thus, the mixing device is supplied to the user in the condition illustrated in FIG. 1, with the slide clamp 24 in its closed condition, pinching closed the flexible tube 14 between bag 2 and vial 4. In this normal condition of the mixing device, membrane 28 covering the wide slot section 26B of the slide clamp 24 is intact, thereby indicating that the slide clamp has never been opened, and therefore, that the materials in bag 2 and vial 4 are in their original unmixed condition.

When it is desired to introduce the contents of vial 4 into bag 2, cap 16 at the end of flexible tube 14 is applied over the mouth of vial 4. This automatically causes cannula 18 to pierce the seal 20 covering the mouth of the vial.

Clamp 24 is then slid to its open position (rightwardly, FIG. 1), to cause the flexible tube 14 to be received within the wide slot section 26B, whereby the flexible tube is no longer pinched closed. Thus, communication is now established between the interior of vial 4 and the interior of bag 2, such that the contents of vial 4 may be added to chamber 6 within bag 2, e.g., by inverting the vial and moving it above the plastic bag, or by squeezing the vial if it is made of flexible plastic material, to pump its contents into chamber 6 of the plastic bag.

After the contents of vial 4 have thus been added to the contents of plastic bag 2, the plastic bag may then be kneaded to uniformly mix the two materials together, before the mixture is administered via flexible tube 22 to the patient.

It will be seen that when clamp 24 has been moved to its open position by causing flexible tube 14 to move into the wide slot section 26B of the clamp, this will also automatically pierce membrane 28. This membrane will therefore show at all times thereafter that the clamp has been moved to its open position, even should the user move the clamp back to its closed position by moving it leftwardly in FIG. 1. Thus, if the user sees that the clamp 24 is in its closed condition and that its membrane 28 is intact, the user is thereby assured that the clamp has never previously been opened, and therefore that the contents of the vial 4 and plastic bag 2 are in their original, unmixed condition.

The break-away valve 30 provides additional protection against mixing of the two materials before the desired time, and additional assurance that the materials are in their original unmixed condition. Thus, when valve 30 is in its normal, closed condition, its membrane 32 blocks the passage of any material via flexible tube 14; and when the valve has been broken away to its open position, the membrane 32 is ruptured to thereby indicate this fact should the valve be reclosed. While this additional protection is desirable, it is not essential, and therefore break-away valve 30 may be omitted, especially where it may be desirable to permit a higher rate of flow and to avoid the possibility of particulate matter from the break-away valve being introduced into the mixed materials.

Figure 2:
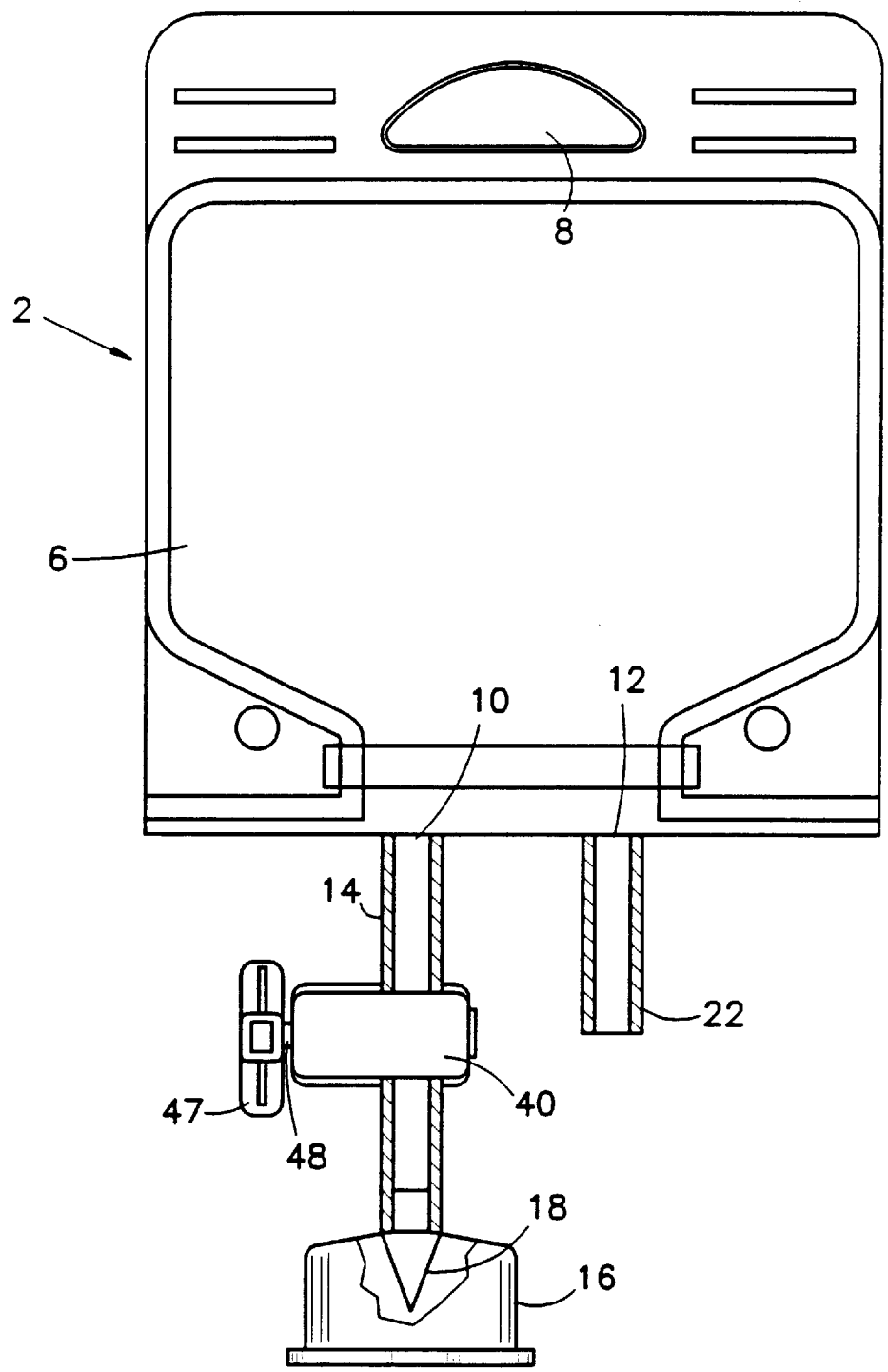
FIG. 2 illustrates a second form of mixing device constructed in accordance with the invention.

FIG. 2 illustrates a variation wherein, instead of using a slide clamp 24 for closing flexible tube 14, a hinge clamp, generally designated 40, is used for this purpose.

Except for this difference, the mixing device illustrated in FIG. 2 is essentially the same and operates in essentially the same manner as described above with respect to FIG. 1, and therefore the corresponding parts have been correspondingly numbered to facilitate understanding.

Figure 3:
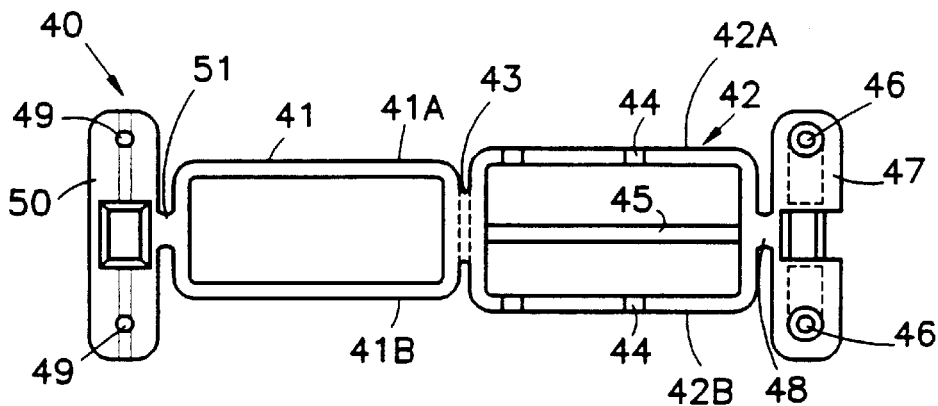
FIGS. 3 and 4 are plan and sectional views, respectively, illustrating the clamp in the mixing device of FIG. 2 while the clamp is in its open condition.
Figure 4:
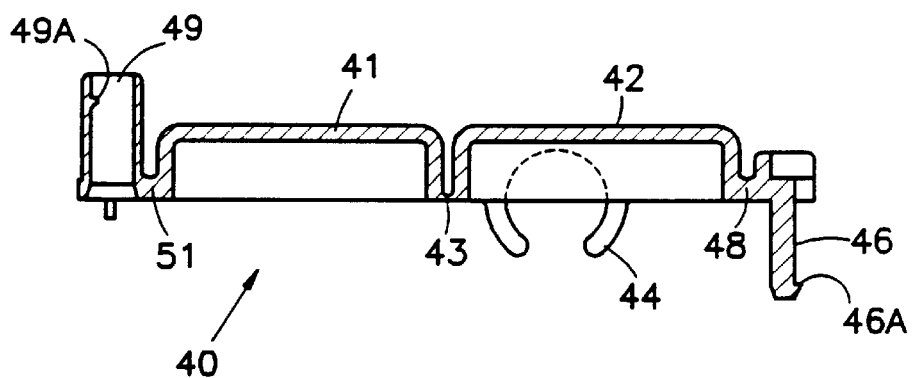
Figure 5:
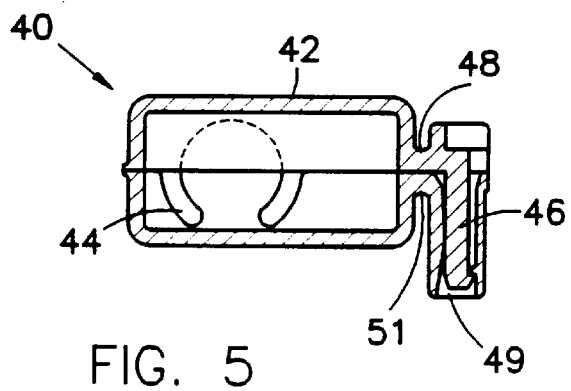
FIG. 5 is an end view illustrating the clamp of FIGS. 3 and 4 in its closed condition.

The structure of the hinge clamp 40 is more particularly illustrated in FIGS. 3–5. It is made of plastic material, e.g., by injection molding, and includes two parts 41, 42 joined together by an integral hinge 43 permitting the two parts to be moved to either an open position as illustrated in FIGS. 3 and 4, or to a closed position as illustrated in FIG. 5.

Part 42 includes a pair of clips 44 on the opposite sides of the part for gripping the flexible tube 14 when the two parts are in their closed positions. Part 42 further includes a rib 45 extending midway between the two clips 44, and transversely to their common axis. Rib 45 serves as a pinching element for pinching the flexible tube between it, walls 42A, 42B of part 42, and walls 41A, 41B of part 41, when the two parts 41, 42 are moved to their closed positions.

The hinge clamp 40 further includes locking elements which lock the two parts in their closed positions, and which are severed when the two parts are first moved from their closed positions to their open positions. These locking elements are constituted of a pair of barbs 46 carried at the opposite ends of a strip 47 joined to part 42 by means of a severable web 48, which barbs are adapted to be received in a pair of sockets 49 formed in a strip 50 joined to part 41 by another severable web 51. Thus, when the two parts are moved to their closed positions (as illustrated in FIG. 5), barbs 46 of strip 47 are received in sockets 49 of strip 50, such that a flat surface of a shoulder 46A formed at the end of barb 46 engages a flat surface of a shoulder 49A formed in the respective socket 49 and thus locks the barb within the socket and prevents its removal.

When the two parts 41, 42 of the hinged clamp 40 are closed and locked in their closed positions, the only way of reopening them is to sever the two strips 47 and 50 from their respective parts 42, 41, along their severable webs 48, 51, which can be done by simply pulling or twisting the webs. Thus, once the two parts of the hinge clamp 40 have been opened, this fact will be readily apparent to the user, and the clamp cannot thereafter be reclosed.

Accordingly, as in the mixing device described above with respect to FIG. 1, the mixing device of FIGS. 2–5 may also be supplied with the hinge clamp 40 in its closed condition as illustrated in FIG. 5. When the two parts are in their closed positions, they are locked in this position by the barbs 46 being received within sockets 49. In order to open the clamp, it is necessary to sever the two strips 47, 50, carrying the barbs 46 and sockets 49, along their webs 48, 51, which can easily be done by twisting the two strips. Accordingly, when the user wishes to use the mixing device, the user would twist the two strips 47, 50 to sever them along their webs 48, 51, thereby permitting the two parts 41, 42 to be moved to their open positions. Since the severing of the two strips 47, 50 will also prevent reclosing of the hinge clamp, this provides assurance to the user that the content of the plastic bag 2 is in its original condition and has not yet been opened.

It will thus be seen that both of the embodiments of the invention described above provide mixing devices which enable materials to be mixed in an efficient and facile manner while maintaining sterile conditions where necessary, and which also provides protection against tampering before use. In addition, both devices are of relatively simple construction which can be produced in volume and at low cost.

While the invention has been described with respect to two preferred embodiments, it will be appreciated that these are set forth merely for purposes of example, and that many other variations, modifications and applications of the invention may be made.

What is claimed is:

1. A mixing device for mixing first and second materials, comprising:

a container for receiving said first material and having an inlet port and an outlet port;

a flexible tube having one end connected to said inlet port;

a cap secured to the opposite end of said flexible tube for attachment to a second container receiving said second material;

and a clamp carried by said flexible tube and normally pinching said flexible tube closed, but being manually openable to permit, when said cap has been attached to said second container, the addition of the second material in said first container to said first material in said second container and mixing of the two materials together in said first container, wherein said clamp is a slide clamp which includes an indicator element which indicates whenever said clamp has been once opened.

2. The mixing device according to claim 1, wherein said clamp includes a severable element which is severed when the clamp is opened thereby preventing reclosing of the clamp.

3. The mixing device according to claim 1, wherein said slide clamp is formed with a slot slidably receiving said flexible tube; said slot including a narrow section which pinches said flexible tube closed when receiving the flexible tube, and a wide section which opens said flexible tube when receiving same; said indicator element being carried by said wide section of the slot and being ruptured by said flexible tube when the flexible tube is received within said wide section of the slot.

4. The mixing device according to claim 3, wherein said indicator element is a membrane covering said wide section of the slot and ruptured when the slide clamp is moved to receive the flexible tube in said wide section of the slot.

5. The mixing device according to claim 1, wherein said clamp is a hinge clamp integrally formed of plastic with two parts hinged together to either a closed position pinching said flexible tube closed, or to an open position opening said flexible tube.

6. The mixing device according to claim 5, wherein said hinge clamp further includes locking elements which are severed when the two parts are first moved from their closed positions to their open positions.

7. The mixing device according to claim 6, wherein said locking elements include a barb joined to one part by a first severable web, and a socket joined to the other part by a second severable web, such that the barb is non-removably received within said socket when the two parts are in their closed positions, requiring severing of said webs in order to open the two parts, thereby preventing reclosing of the two parts.

8. The mixing device according to claim 7, wherein said one part includes two barbs joined to said one part by said first severable web, and said other part includes two sockets joined to said other part by said second severable web.

9. The mixing device according to claim 1, wherein said first container is a pliable bag permitting mixing the two materials when introduced therein by kneading the bag.

10. The mixing device according to claim 1, wherein said cap includes a cannula communicating with said flexible tube, which cannula automatically pierces a seal in said second container when the cap is attached thereto.

11. The mixing device according to claim 1, wherein said flexible tube further includes a break-away valve which is normally closed, but which may be broken away to open the valve.

* * * * *